United States Patent [19]

Farquharson et al.

[11] Patent Number: 4,666,706

[45] Date of Patent: May 19, 1987

[54] DELAYED RELEASE INSECTICIDAL COMPOSITION AND METHOD OF MAKING SAME

[75] Inventors: Richard A. Farquharson, Angleton, Tex.; Robert L. Reierson; Kenneth A. Burdett, both of Midland, Mich.

[73] Assignee: The Dow Chemical Company, Midland, Mich.

[21] Appl. No.: 800,621

[22] Filed: Nov. 21, 1985

[51] Int. Cl.⁴ .................. A01N 25/34; A61D 9/00; A61K 31/74; A01M 1/20

[52] U.S. Cl. .................................. 424/408; 424/412; 424/78

[58] Field of Search .................. 424/21, 29, 79, 78

[56] References Cited

U.S. PATENT DOCUMENTS

| | | | |
|---|---|---|---|
| 3,620,453 | 11/1971 | Gancberg et al. | 424/21 |
| 3,864,468 | 2/1975 | Hyman et al. | 424/29 |
| 4,007,258 | 2/1977 | Cohen et al. | 424/81 |
| 4,162,165 | 7/1979 | Schwab | 106/21 |
| 4,195,154 | 3/1980 | Kaiser et al. | 528/98 |
| 4,198,782 | 4/1980 | Kydonieus et al. | 424/16 |
| 4,303,642 | 12/1981 | Kangas | 424/78 |
| 4,320,113 | 3/1982 | Kydonieus | 424/78 |
| 4,439,415 | 3/1984 | Hennart et al. | 424/21 |

*Primary Examiner*—Douglas W. Robinson

[57] ABSTRACT

A chemical complex of a biocidal agent such as orthophenylphenol and chlorpyrifos and a non-ionic polymer of 2-ethyl oxazoline (PEOx). The complex is compatible with and contained in a plastic film such as polyethylene, polypropylene and poly(vinyl chloride) and the product is characterized by a reduced rate of release of the biocide without adversely affecting either the properties of the biocide or the film itself. The biocide-impregnated plastic finds utility in bags and in packing used to inhibit fungicidal growth and to prevent attack by insects and bacteria during growing, drying, packing, shipping, storage and marketing of fruits and vegetables.

2 Claims, No Drawings

DELAYED RELEASE INSECTICIDAL COMPOSITION AND METHOD OF MAKING SAME

BACKGROUND OF THE INVENTION

The present invention relates to slow release insecticidal and fungicidal chemical agents incorporated in thermoplastic materials. More particularly, the invention is directed to complexes of non-ionic polymers of 2-ethyl oxazoline (PEOx) with biocides such as ortho-phenylphenol and chlorpyrifos and dispersed in thermoplastic polymeric films and pellets to achieve a reduction in the rate of release of the biocide from the plastic carrier.

It is known in the prior art to incorporate biocidal agents such as chlorpyrifos insecticide into plastic film convertible to bags to protect bananas during their growth period. It is known, as well to impregnate plastic film with ortho-phenylphenol for fungicidal protection.

In such applications, the need for and the desirability of reducing the rate of release of fungicides such as ortho-phenylphenol (O-PP) from film or from plastic pellets so as to achieve long term efficacy is known. A variety of different agents including chelants, complexing agents and other chemicals have been proposed as means to achieve this goal. The concept of utilizing specialized biocidal and fungicidal agents in plastic compositions has found broad acceptance. Extensive research has been conducted to discover and develop products in which the biocidal and fungicidal agents are released from plastic films and from plastic pellets under controlled conditions and over extended time periods. The present invention constitutes an important contribution to this field of research and investigation.

SUMMARY OF THE INVENTION

The present invention provides an improved controlled-release biocidal product constituting a complex of a non-ionic polymer of 2-ethyl oxazoline (PEOx) and selectable biocidal agents including ortho-phenylphenol and chlorpyrifos in a thermoplastic carrier polymer film or pellets, such as polyethylene, polypropylene and poly(vinyl chloride).

It is an important feature of the compositions of the invention that they ensure release of the active agents over significantly extended useful time periods.

A related feature of the invention is that the complexes exhibit enhanced stability as compared with prior art preparations, and are characterized by their compatibility with thermoplastic polymers including polyethylene, polypropylene and poly(vinyl chloride).

Yet another important advantage of the products of the invention is that the polymers of 2-ethyl oxazoline used in the complex are non-volatile and are essentially biologically inert.

The invention provides a method of incorporating in a variety of thermoplastic materials biocidal agents complexed with polymers of 2-ethylene-oxazoline to provide controlled release of the active biocidal agent over time periods which are significantly longer than those heretofore achieved.

DETAILED DESCRIPTION OF PREFERRED EMBODIMENTS

The present invention provides stabilized biocidal preparations constituting complexes, in plastics, and methods for making such preparations. The activity of the biocidal agent in the plastic carrier remains unimpaired, and the effective time period of the utility of the active agents is significantly extended. The products of the invention provide protection for fruits and vegetables, etc., over their entire growing season, as well as in subsequent storage, shipping, packaging and marketing.

The products of the invention include plastic films and pellets impregnated with slowly released bactericidal, fungicidal, and insecticidal compositions useful to protect grapes, plums and other fruit against mold and fungus attack during solar drying operations. The pellets or films may also be incorporated directly in boxes, crates and other containers for controlling insect infestation.

Preferred embodiments of the active compositions are polymers of or complexes of 2-ethyl oxazoline (PEOx) with biocides including ortho-phenylphenol, and chlorpyrifos in a carrier film such as polyethylene, polypropylene, and poly(vinyl chlroide).

When incorporated into plastic conduits or pipes, the compositions of the invention provide protection against attack by ants and termites.

A detailed description of a method for preparing a preferred complex of the invention is set forth below. The example is illustrative only, and is not to be construed in any limiting sense.

EXAMPLE 1

Preparation of 2:1 Molar Complex of Poly(ethyl oxazoline and Ortho-phenylphenol

To a 100 ml. round bottom flask was added 50 cc. of methanol, and 16 g of 50M. poly(ethyl oxazoline) (PEOx) of 50,000 molecular weight. The resulting mixture was stirred until the solid dissolved. To this solution was then added 13.8 g (0.081 mole) of o-phenylphenol (O-PP). When the ortho-phenylphenol dissolved, the resulting clear solution was concentrated on a rotoevaporator to about 70% solids. The clear viscous liquid was used directly in incorporating the complex into polyethylene plastic, as described herebelow.

Compounding Procedure

A Brabender mixer was heated to 160° C. and about 40 grams of low-density polyethylene (LDPE) 750, M.I. 6.0, was placed in the mixing head rotated at about 63 R.P.M. When the pellets became molten, 1.36 g of the 70% solids solution of the 2:1 complex was added, while mixing. The remainder (3 g) of the low-density polyethylene was then added. The total solids charge in the mixing head was 44 g. The mixer was operated for ten minutes after the torque had leveled off (approximately 13 minutes total mixing time). The hot melt was then removed from the head and cut into relatively small particles or chunks. These chunks (0.2 g) were then pressed into a 2"×2"×1 mil transparent film. The conditions for the Pasadena hydraulic press used were 3 minutes at about 150° C., 8,000 psig; 3 min. at 150° C.; 30,000 psig, and 7 min., 30,000 psig cool.

U.V. Biocide Release Rate Measurement

The 2"×2"×1 mil P.E. film was cut into a ½"×2"×1 mil strip. The absorbance of the film at 285 mu was determined at various times to establish the remaining concentration of ortho-phenylphenol as a function of time, the equation relied upon being the following:

%O-PP Remaining = 100×(A$_T$-B)/(A$_o$-B)

where
A = Initial absorbance (determined <15 min. after pressing film).
B = Absorbance of a 1 mil P.E. film containing the same wt. % PEOx as the film being analyzed.
A$_T$ = Absorbance of the O-PP containing film at time T.

TABLE 1

% O-PP Remaining by U.V. Analysis

| | Mole Ratio PEOx/OPP | Half Life In Days |
|---|---|---|
| 50 M PEOx | 2/1 | 3 |
| | 5.9/1 | 88% remaining at 22 days |
| | 8.6/1 | 81% remaining at 14 days |
| | 10.6/1 | 88% remaining at 22 days |
| 500 M PEOx | 2/1 | 14 |
| | 5.9/1 | <1 |
| | 10.6/1 | 1 |

EXAMPLE 2

An alternate method of compounding the products of the invention is set forth below:

Approximately 1.0 part of the complex was blended into 99 parts by weight of molten low-density polyethylene (melt index, 6.0; density 0.9244 with 1300 ppm erucamide and 4000 ppm SiO$_2$) at 150° C. on a roll mill. The mixture was cooled, chopped, extruded at 150° C. barrel temperature through a 1" Killion extruder, and then pelletized. The resulting pellets were then re-extruded to produce 1 mil (0.001 in.) thick tubular film for testing.

Measurement of Rate of Release of Biocide

Approximately 1.0 g of the freshly extruded film was extracted with 20 ml. chloroform overnight. The absorbance of the extract scanned from 360 to 240 nanometers was compared with that of calibration standards so as to determine quantitatively the amount of biocide extracted. The remaining film was suspended on a lattice rack at ambient laboratory conditions (21°-23° C.) and sampled periodically to follow the reduction in biocide content as a function of time. Concentration vs. time was then plotted and the half-life calculated. Values for the complexes tested are summarized in Table 2.

TABLE 2

Half-Life For Release of Biocide Complexes in 1 mil Polyethylene Film

| Biocide | Complex Additive | % Biocide Wt. | % Biocide Molar | Half-Life (HR) |
|---|---|---|---|---|
| o-pp | — | 100 | 100 | [3–6] |
| *****o-pp | Bardac ® 2250 | 32 | 50 | [96–140] |
| o-pp | 5-Ethyl-2-oxazolidinone | | | <8 |
| o-pp | Poly(3-vinyl-5-methyl-2-oxazolidinone) | | | <8 |
| o-pp | PEOx (200,000 Mol. Wt.) | 46 | 33 | 50–51 |
| *o-pp | PAMAM | 50 | 40 | 8 |
| **o-pp | XD-30643.14 | 29 | 37 | 4 |
| ***o-pp | CALGON ® 261 | 51 | 37 | 7 |
| ****o-pp | XD-30269.01 | 47 | — | 3 |
| Cl—Py | — | 100 | 100 | 48–60 |
| Cl—Py | PEOx (200,000 Mol. Wt.) | 64 | 33 | 170–187 |

*
**Poly(((2-hydroxy-3-(trimethylammonio)-1,2-ethanediylimino (1-oxo-1, 3-propanediyl) 2) chloride
***Poly(dialkylamine) (tetra ammonium salt)
****PURIFLOC C31 + Quat 188
*****didecyldimethyl ammonium chloride The complexes of poly(ethyl oxazoline) and ortho-phenylphenol of the invention are glassy solids. It has been found that these products are conveniently handled in 10% to 30% of solvent. The ratio of the polymer and the ortho-phenylphenol may range from 1:99 to 99:1, the optimum concentrations for any particular application varying depending upon the desired rate of release and the level of ortho-phenylphenol necessary to achieve the desired fungicidal activity.

What is claimed is:

1. A slow release insecticidal and fungicidal composition comprising a complex of a non-ionic polymer of 2-ethyl oxazoline of a molecular weight of about 50,000 to about 200,000 with a biocidal agent selected from the group consisting of ortho-phenylphenol and chlorpyrifos, said polymer being distributed throughout a thermo-plastic carrier polymer selected from the group consisting of polyethylene, polypropylene, and poly(vinyl chloride), and the ratio of the polymer of 2-ethyl oxazoline to biocidal agent being from 1:99 parts by weight to 99:1 parts by weight, to provide controlled release of said biocidal agent from said thermo-plastic carrier polymer.

2. A process for preparing an insecticidal and fungicidal composition comprising a complex of a non-ionic polymer of 2-ethyl oxazoline and a biocidal agent for release of said biocidal agent over an extended time period, said method comprising the steps of:
dissolving poly-ethyl oxazoline of a molecular weight of about 50,000 to about 200,000 in an organic solvent and adding thereto a biocidal agent selected from the group consisting of ortho-phenylphenol and chlorpyrifos to form a complex with the poly-ethyl oxazoline,
mixing the complex thus formed with an organic thermo-plastic carrier polymer selected from the group consisting of polyethylene, polypropylene, and poly(vinyl chloride) to provide a dispersion of the complex in the carrier polymer, and
recovering the organic thermo-plastic carrier polymer containing the complex wherein the ratio of the polymer of 2-ethyl oxazoline to biocidal agent is from 1:99 parts by weight to 99:1 parts by weight.

* * * * *